United States Patent [19]

Baylink

[11] Patent Number: 5,071,655

[45] Date of Patent: * Dec. 10, 1991

[54] PHARMACEUTICAL COMBINATION FOR TREATMENT OF BONE-WASTING DISEASES

[76] Inventor: David J. Baylink, 1534 Fern Ave. West, Redlands, Calif. 92373

[*] Notice: The portion of the term of this patent subsequent to Mar. 27, 2007 has been disclaimed.

[21] Appl. No.: 464,225

[22] Filed: Jan. 12, 1990

[51] Int. Cl.$^5$ .................. A61F 13/00; A61K 33/16; A61K 31/415
[52] U.S. Cl. .................. 424/422; 424/434; 424/449; 424/464; 424/606; 424/673; 514/389
[58] Field of Search .............. 424/422, 434, 449, 464, 424/673, 675, 676; 514/241, 252, 255, 277, 389, 391, 383

[56] References Cited

U.S. PATENT DOCUMENTS

| | | | |
|---|---|---|---|
| 4,386,100 | 5/1983 | Brittain et al. | 514/389 |
| 4,501,754 | 2/1985 | Wechter et al. | 514/456 |
| 4,686,104 | 8/1987 | Bockman et al. | 424/131 |
| 4,726,952 | 2/1988 | Walsdorf et al. | 424/476 |

*Primary Examiner*—Thurman K. Page
*Assistant Examiner*—G. S. Kishore
*Attorney, Agent or Firm*—Cooley, Godward, Castro, Huddleson & Tatum

[57] ABSTRACT

A pharmaceutical composition for increasing bone mass and preventing loss of bone mass is provided, comprising a fluoride source and a mitogenic hydantoin in combination with a pharmaceutically acceptable carrier, in which the fluoride source provides a molar ratio of fluoride ion to hydantoin in the composition of from about 0.1:1 to about 100:1. The combination is administered to a vertebrate, typically in the form of an orally administratable tablet or capsule.

18 Claims, No Drawings

PHARMACEUTICAL COMBINATION FOR TREATMENT OF BONE-WASTING DISEASES

FIELD OF THE INVENTION

This invention is related to compositions used in the treatment of bone-wasting diseases (osteopenias), particularly fluoride-containing compositions.

BACKGROUND OF THE INVENTION

Bone formation in vertebrates is a dynamic process, involving continuous production of bone and continuous bone resorption. Osteopenia is a general term used to describe any bone-wasting disease in which the rate of bone resorption is greater than the rate of bone formation. Osteoporosis, a bone-wasting disease characterized by a net loss of bone mass due to increased bone resorption exceeding bone formation, is a common disorder affecting millions of people throughout the world. In osteoporosis, the skeleton become weakened and unable to bear the normal stresses imposed on it. The effects of the disease are therefore generally seen in the parts of the skeleton that are weight-bearing, especially the spine and hips, which can fracture in the absence of trauma.

Among the drugs that have been used to treat bone-wasting diseases is sodium fluoride, which has been shown to stimulate bone formation in vivo by a direct mitogenic effect on bone cells. Bone mineral density of the axial skeleton of patients treated with fluoride increases, and the serum alkaline phosphatase level, an index of bone formation in the skeleton, also increases. Significant increases in spinal bone density are seen after about 12-18 months of fluoride therapy. However, fluoride treatment is not equally effective in all patients, as some patients respond poorly to fluoride (showing only small increases in bone mineral density) and others do not respond at all.

Dilantin (also known as phenytoin or diphenylhydantoin) is a known anti-convulsant drug used extensively in the treatment of grand mal and psychomotric epilepsy. Clinical data relating dilantin to effects on bone are mixed. Some studies in mouse calvaria in culture have shown a stimulation of fibroblast proliferation and an ability to inhibit parathyroid hormone and prostaglandin E2-stimulated bone resorption. One study of patients on dilantin therapy also indicated significantly less mean bone loss than a control group of patients receiving no dilantin. However, other studies have shown that dilantin can actually cause osteoporosis, perhaps by producing vitamin D deficiency. Accordingly, the effects of dilantin on net bone formation or loss are inclusive.

In addition to fluoride treatment, there are a number of other techniques that have been suggested for increasing bone mass, including use of 1,25-dihydroxy vitamin D and other growth-promoting substances, but these treatments have met with mixed success.

A number of these problems were overcome by an invention previously made by the present inventor and described in U.S. Pat. application Ser. No. 07/080,759, filed Aug. 3, 1987, now a U.S. Pat. No. 4,911,931 which is herein incorporated by reference. That earlier invention provides a pharmaceutical composition useful for increasing bone mass and/or preventing loss of bone mass in vertebrates. The composition comprises a fluoride source and a mitogenic hydantoin (typically a 5-aromatic-substituted hydantoin) in combination with a pharmaceutically acceptable carrier. By providing a hydantoin in combination with a fluoride source, significant increases are seen in bone formation over untreated controls or controls treated with fluoride alone. Additionally, the combination has been shown to improve spinal bone density in all patients treated, including those who are normally poor responders to fluoride alone.

However, it was thought when the earlier application was filed that a molar ratio of fluoride (not fluoride source, since the fluoride source does not necessarily produce only one fluoride ion per molecule) to the hydantoin of at least 1:1 was required in order to produce the desired increase. There does not appear to be any upper limit on the molar ratio of fluoride ion to hydantoin, although typically the molar ratio will be less than 1000:1. It is has now been discovered that lower ratios of fluoride to hydantoin are effective and may be used, particularly in view of the tendency toward administering lower amount of fluoride in order to avoid adverse side effects.

Accordingly, there remains a need for a practical pharmaceutical composition capable of increasing the rate of bone formation, particularly a composition that is effective on patients that are normally not responsive to treatment with fluoride, which uses relatively low levels of fluoride.

SUMMARY OF THE INVENTION

The present invention provides a pharmaceutical composition useful for increasing bone mass and/or preventing loss of bone mass in vertebrates. The composition comprises a fluoride source and a mitogenic hydantoin (typically a 5-aromatic-substituted hydantoin) in combination with a pharmaceutically acceptable carrier. The molar ratio of fluoride ion to hydantoin is from about 0.1:1 (1:10) to about 100:1. Compositions at the lower end of this range (i.e., less than 1:1) lessen the side effects of fluoride and allow the use of higher levels of hydantoin (such as when a patient becomes acclimated to a particular dose of the hydantoin). By providing a hydantoin in combination with a fluoride source, significant increases are seen in bone formation over untreated controls or controls treated with fluoride alone.

DESCRIPTION OF SPECIFIC EMBODIMENTS

The present invention provides a method of increasing the rate of bone formation and a pharmaceutical composition that has this effect. Specifically, the method comprises administering a combination of a fluoride ion source and a 5-aromatic-substituted hydantoin to a vertebrate, in which the fluoride source provides a molar ratio of fluoride ion to hydantoin of from about 0.1:1 (1:10) to about 100:1. The minimum amount of the combination necessary to achieve the desired result varies from species to species and within a species from one individual to another in accordance with the normal variation in responses. However, it is possible to achieve an increase in the rate of bone formation in all individuals to whom the composition of the invention is administered by adjusting the total amount of the composition administered to the individual.

The two principal components of the composition are a fluoride source and a 5-aromatic-substituted hydantoin. The fluoride source can be any source of fluoride ions present in a form from which fluoride ions can be released when administered to a subject. For example, an alkaline metal fluoride salt, an alkaline earth metal fluoride salt, an alkaline metal monofluorophosphate salt, or an alkaline earth metal monofluorophosphate salt can be used. It is recognized that some such materials, such as calcium fluoride, are insoluble and do not by themselves represent direct sources of soluble fluoride ions. However, other agents can be included in the composition to assist in dissolution or breakdown of the fluoride source in order to provide soluble fluoride ions. For example, a calcium chelator can be provided to assist in solubilizing calcium fluoride. However, soluble fluoride sources, such as alkaline metal fluoride salts and alkaline metal monofluorophosphate salts, are preferred, particularly sodium and potassium salts.

It is recognized that a number of fluoride compounds are toxic, at least to some extent. For example, sodium hexafluorosilicate is a rat poison. However, it is also recognized that many toxic compounds can be used therapeutically if the dose is carefully controlled to provide a therapeutic effect the benefits of which outweigh the toxic effects. Example of known fluoride-containing compounds that are both toxic and therapeutic include niflumic acid and flufenamic acid (both of which are anti-inflammatory agents), flumetramide (a skeletal muscle relaxant), and stannous hexafluorozirconate and stannous fluoride (both of which are anti-carries agents use in toothpaste). These and numerous other compounds or compositions that contain a significant amount of fluoride (such as ammonium hexafluorophosphate, which contains 66.9% fluoride) and sodium borofluoride (a fluorinating agent for water also known as fluoroborate) can also be used if the dosage is adjusted to provide for the desired therapeutic benefit. The most preferred fluoride source is sodium monofluorophosphate, particularly in a composition that is enteric coated or formulated as a time-release formulation, both of which act to provide lower gastro-intestinal side effects and higher tolerance to the fluoride source.

The word "hydantoin" in general usage can refer either to the specific compound known as hydantoin or to a compound having the hydantoin ring structure with various substituents. Hydantoin is used in this latter sense throughout the present specification. The hydantoin ring system is shown below:

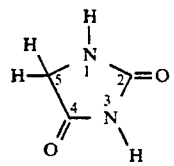

The ring numbering system is shown by numbers inside the ring. Compounds useful in the practice of the invention have mitogenic activity and often have an organic substituent comprising an aromatic ring at the 5 position. The aromatic ring is typically a 5- or 6-membered ring containing 0-3 nitrogen ring atoms or 0-1 oxygen or sulfur ring atoms. Five-membered rings provide the necessary electrons for aromaticity. Six-membered rings can contain, but are not required to contain, heteroatoms. Examples of 5-membered aromatic ring systems are furan, thiophene, pyrrole, pyrazole, 1,2,3-triazole, 1,2,4-triazole, isoxazole, oxazole, thiazole, isothiazole and the like. Typical 6-membered aromatic rings are benzene, pyridine, pyridazine, pyrimidine, pyrazine, s-triazine, as-triazine, v-triazine and related compounds. Compounds containing a single benzene ring are preferred. The organic substituent can be attached either directly to the hydantoin ring or can be attached through an intervening hydrocarbyl group (which may be substituted), typically a $C_1$-$C_3$ alkylene bridge. Direct attachment of the aromatic ring to the hydantoin (e.g., as a phenyl substituent) is preferred. The aromatic ring can be substituted with typical substituents found thereon, including but not limited to $C_1$-$C_4$ hydrocarbyl, hydroxy, carboxy, amino, $C_1$-$C_4$-hydrocarbyl-substituted (or disubstituted) amino, halo, nitro, and carboxyl. Particularly preferred are phenyl and para-hydroxyphenyl substituents.

Either one or two of the hydrogens present at C5 of the hydantoin ring can be an organic substituent comprising an aromatic ring. The other substituent on the same as or different from the first aromatic ring) or a $C_1$-$C_4$ hydrocarbyl group or hydrogen. The substituent on N1 can be a $C_1$-$C_4$ hydrocarbyl group or hydrogen and typically is hydrogen. The substituent on N3 can also be a $C_1$-$C_4$ hydrocarbyl group or hydrogen. When an alkyl group is present at this position, the resulting hydantoin often has a sedative effect. When the substituent on N3 is hydrogen, sedative effects are generally lacking. Substituents providing mitogenic activity to the hydantoin yet lacking in sedative activity are generally preferred.

Compounds of the invention can also be pharmaceutically acceptable salts of the hydantoins. For example, alkaline metal salts can readily be prepared by using the weakly acidic properties of the hydrogen on N3, which is situated between two carbonyl groups. The resulting compound is often written as an enol salt, the carbonyl at C2 participating in formation of the enol. Sodium salts are preferred.

Specific hydantoins include compounds of the formula:

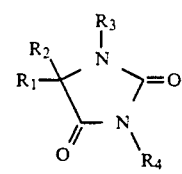

wherein $R_1$ is an organic substituent comprising a 5- or 6-membered aromatic ring containing 0-3 nitrogen ring atoms or 0-1 oxygen or sulfur ring atoms; $R_2$ is $R_1$, a $C_1$-$C_4$ hydrocarbyl group or H; $R_3$ is a $C_1$-$C_4$ hydrocarbyl group or H; and $R_4$ is a $C_1$-$C_4$ hydrocarbyl group or H; or a pharmaceutically acceptable salt thereof. Hydro-carbyl groups include alkyl, alkenyl, and alkynyl groups and can be either straight chained or branched. Methyl and ethyl groups are preferred.

As an alternative to providing a separate fluoride source and hydantoin, it is also possible to provide the hydantoin with a fluoride substituent that can be hydrolyzed or otherwise released in vivo. For example, an alkyl fluoride substituent, such as fluoromethyl, can be provided. Such a substituent will provide fluoride ions by hydrolysis of a fluoride in a biological fluid.

In addition to the two principal active components, a composition can be prepared containing other active ingredients known to have a desirable effect in bone disorders, such as 1,25-dihydroxy vitamin D. A combination comprising 1,25-dihydroxy vitamin D in addition to the two previously disclosed active ingredients is specifically contemplated. In a composition intended for use in post-menopausal women, the composition can also contain an estrogen.

A composition of the invention will also contain a pharmaceutically acceptable carrier. By this is meant an inert solid or liquid material, which may be inorganic or organic and of synthetic or natural origin, with which the active components are mixed or formulated to facilitate administration to a subject. Any of the materials customarily employed in formulating pharmaceuticals are suitable. Suitable solid carriers include natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites, and micas; calcium carbonate; calcium sulfates; synthetic hydrated silicon oxides and synthetic calcium or aluminum silicates; elements such as carbon or sulfur; natural and synthetic resin such as polyvinyl alcohol; and waxes such as paraffin and beeswax. Examples of suitable liquid carriers include water and aqueous solutions containing oxygenated organic compounds such as ethanol.

Numerous other pharmaceutically acceptable components such as ingestible dyes, dispersing agents, flavors and the like can be included in the composition. The composition can be prepared either in a quick-release or in a time-release form. Enteric coatings can be used if desired but are not required. However, enteric coatings are desirable for use with some fluoride sources, as previously discussed, in order to alleviate adverse gastro-intestinal effects.

Compositions of the invention will generally comprise 5-95% active ingredients and 95-5% carrier by weight. A similar range of weight ratios of active ingredients to each other generally also occurs, from 5-95% of the composition by weight being the fluoride source and 95-5% by weight being the hydantoin. However, it is preferred to provide a molar ratio of fluoride (not fluoride source, since the fluoride source does not necessarily produce only one fluoride ion per molecule) to the hydantoin of at least 0.1:1 (1:10). There does not appear to be any upper limit on the molar ratio of fluoride ion to hydantoin, although typically the molar ratio will be less than 1000:1, preferably less than 100:1, more preferably less than 50:1, even more preferably less than 25:1, most preferably less than 12:1.

The method of the invention appears to be useful for any vertebrate and therefore will find use in both the human and veterinary fields. The combination of the invention has proven useful in treating slow-healing or non-healing fractures and has produced fracture healing even when fractures were not healed after treatment with fluoride alone. The method and composition will find particular use as a feed supplement with fowl, particularly chickens and turkeys (especially turkeys), since breeding programs have produced chickens and turkeys with weak bone structure for their current body weights.

Another primary use is with humans. The composition can be used to treat osteopenias, particularly osteoporosis.

The combination of the invention is typically administered orally since both fluorides and hydantoins can be absorbed in this manner without being degraded. In fact, intestinal enzymes are used to break down some fluoride sources, such as sodium monofluorophosphate, to provide fluoride ions. However, parenteral injection is also a suitable route of administration if the fluoride source is selected for this purpose. Transdermal, subcutaneous (slow-release) pellets, and nasal administrations are also possible as is intravenous administration. Total parenteral nutrition solutions can be used as vehicles to administer a combination of the invention into the small bowel through a semi-permanent tube placed in an incision in the abdominal wall. This route has in the past been shown to avoid gastro-intestinal distress for fluoride ions alone and should be effective as a means of administration of the present combination.

The fluoride source is typically administered in an amount sufficient to provide a dose range of 20-200 $\mu$M fluoride ion at the cellular level. In humans, this corresponds to about 0.1-10 mg fluoride/kilogram of body weight per day. Lower dose rates, for example from 0.01-0.1 mg/kg/day, can be administered as a prophylactic measure. The amount of fluoride source can be calculated from the relative molecular weights of the fluoride source and its fluoride content. For example, the common fluoride source sodium fluoride is commonly administered at a rate in the range of from about 10 mg to about 60 mg per day to an adult human. The hydantoin is typically administered to provide a serum dose range of 1-20 $\mu$g/ml (for dilantin; other hydantoins would be administered at equivalent rates). This typically corresponds to about 0.1-2.0 mmole hydantoin/kilogram of body weight. A composition prepared in unit dosage form will typically contain 5-100 mg fluoride (preferably 10-50 mg) and 25-1000 mg dilantin or the equivalent weight of a different hydantoin (preferably 50-600 mg, more preferably 100-300 mg) in a single tablet, capsule or injectable bolus. For example, the typical hydantoin phenytoin is commonly administered is commonly administered at a rate in the range of from about 50 mg to about 800 mg per day to an adult human.

A single unit dosage can be administered per day or smaller unit dosages can be provided for administration spaced over intervals. The length of time required for determining measurable results is somewhat difficult to determine. Measurable results have been seen in two months, but the optimum time may be either shorter or longer. However, shorter times are expected to be useful since the serum alkaline phosphatase level is already increased after two months of administering the combination of the invention. Serum alkaline phosphatase is a measure of bone-growth activity.

Some side effects of fluoride and dilantin need to be considered in preparing compositions of the invention. The side effects of fluoride include nausea and/or heartburn with sodium fluoride formulations. These side effects are largely abrogated by time-release (enteric-coated) preparations, especially mono-fluorophosphates. Time-release produces diarrhea somewhat more frequently, but the diarrhea is rarely of a magnitude that would warrant discontinuing therapy. Fluoride can also cause athralgias (joint pains), but these are generally self-limited as they disappear when the drug is withdrawn or continued at a lower dose. In summary, neither side effect is of significant magnitude to warrant discontinuing therapy in most patients. Studies indicate that 98% of patients tolerate the fluoride sources well.

Dilantin has a sedative effect (light-headedness and dizziness) in about 25% of patients treated. An additional but less common side effect is nausea. Skin rash may occur, but is very rare. Gingival hyperplasia may occur as well. More gingival hyperplasia may be seen when a combination containing dilantin is administered to patients with osteogenesis imperfecta.

The invention now being generally described, the same will be better understood by reference to the following specific examples which are provided for purposes of illustration only and are not to be considered limiting of the invention unless so specified.

EXAMPLE 1

IN VITRO CELL GROWTH STUDIES

An initial study was performed on isolated embryonic chick calvarial cells grown in monolayer culture. Prior studies had shown that fluoride stimulates tritiated thymidine incorporation by these cells over a dose range of 25-300 $\mu$M when administered as sodium fluoride. The increased thymidine uptake reflects the incorporation of the thymidine into DNA and therefore is a measure of cell proliferative activity.

In the presence of sodium fluoride, 10 $\mu$M dilantin significantly increased thymidine incorporation by the chick calvarial cells not only above control (unstimulated) cultures, but also above the stimulation obtained with fluoride alone. The dilantin-associated stimulation of thymidine incorporation by chick calvarial cells also shows a dose responsiveness. Dilantin over a dose range of 1-30 $\mu$M produced a consistent stimulation of thymidine incorporation into a trichloroacetic acid (TCA) precipitable protein. When sodium fluoride at either 50 or 200 $\mu$M and dilantin were added concurrently to the calvarial cell cultures, the combination produced a marked and significant stimulation of thymidine uptake that was greater not only than that of basal (unstimulated) controls, but also greater than that of dilantin alone. The more fluoride added with the dilantin, the greater the response obtained.

EXAMPLE 2

IN VIVO STUDIES

A study performed in the Osteoporosis Clinic L at Loma Linda University tested osteoporotic female patients who were treated with either 30-40 mg fluoride/day or combinations of fluoride with other drugs. Efficacies were assessed by measuring bone mineral density in the spine by quantitative computed tomography (QCT) before drug treatment and after 12 months of the experimental therapy. The following combinations were examined: (1) fluoride alone; (2) fluoride plus estrogen; (3) fluoride plus 1,25-dihydroxy vitamin D; and (4) fluoride plus dilantin.

Fluoride treatment alone was found to increase spinal bone density (i.e., increase the spinal QCT value) by a mean value of 13 mg/cm$^3$ after 12 months (S.D. 16 mg/cm$^3$, n=60) compared with basal values. The combination therapies of fluoride plus estrogen or of fluoride plus the vitamin D metabolite did not significantly increase the mean change in QCT above this value (12±15 mg/cm$^3$, n=12; and 17±17 mg/cm$^3$, n=8, respectively). In contrast, the combination of fluoride at 30-40 mg/day and dilantin at 100-300 mg/day more than doubled the mean spinal QCT (27±14, n=8). This represents a significant increase in spinal bone density above that seen with fluoride alone within 12 months of treatment.

This experiment also demonstrated that patients who did not respond to fluoride alone were aided by the combination of fluoride and dilantin. The standard deviations of the mean QCT values did not differ between patients treated with fluoride alone and those treated with fluoride and dilantin, indicating that the combination of dilantin and fluoride improves spinal bone density in all patients, including those who are normally poor responders to fluoride.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A pharmaceutical composition for increasing bone mass and preventing loss of bone mass, comprising:
effective amounts of a fluoride source capable of releasing fluoride ions in a physiological environment and a mitogenic hydantoin comprising a hydantoin having an aromatic substituent at position 5 in combination with a pharmaceutically acceptable carrier, wherein said fluoride source provides a molar ratio of fluoride ion to hydantoin of from about 0.1:1 to about 100:1.

2. The composition of claim 1, wherein said fluoride source is an alkali metal fluoride salt, an alkaline earth metal fluoride salt, an alkali metal monofluorophosphate salt, or an alkaline earth metal monofluorophosphate salt.

3. The composition of claim 1, wherein said hydantoin is a compound of the formula:

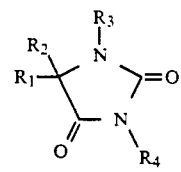

wherein $R_1$ is an organic substituent selected from the group consisting of substituted and unsubstituted 5-and 6-membered aromatic rings containing 0-3 nitrogen ring atoms or 0-1 oxygen or sulphur ring atoms and said aromatic rings are attached to the hydantoin ring of said formula through an intervening substituted or unsubstituted hydrocarbyl group containing from 1 to 3 carbon atoms; $R_2$ is $R_1$, a $C_1$-$C_4$ hydrocarbyl group or H; $R_3$ is a $C_1$-$C_4$ hydrocarbyl group or H; $R_4$ is a $C_1$-$C_4$ hydrocarbyl group or H; or a pharmaceutically acceptable salt thereof.

4. The composition of claim 3, wherein said fluoride source is a sodium salt and in said hydantoin $R_1$ comprises a phenyl or a phenyl substituted with a $C_1$-$C_4$ alkyl, hydroxyl, carboxyl or amino group or an amino group substituted with one or two $C_1$-$C_4$ alkyl groups; $R_2$ is $R_1$, a $C_1$-$C_4$ alkyl group or H; $R_3$ is H; and $R_4$ is a $C_1$-$C_4$ alkyl group or H; or a pharmaceutically acceptable salt thereof.

5. The composition of claim 4, wherein $R_1$ is phenyl or said substituted phenyl; $R_2$ is $R_1$, a $C_1$-$C_4$ alkyl group or H; and R₄ is methyl, ethyl or H; or a lithium, sodium or potassium salt thereof.

6. The composition of claim 5, wherein said hydantoin is phenytoin, phenytoin sodium, mephenytoin or ethotoin.

7. The composition of claim 6, wherein said fluoride source is NaF or Na₂PO₃F.

8. The composition of claim 1, wherein said composition comprises 5-95% active ingredients and 95-5% of said carrier, wherein said active ingredients comprise 5-95% of said fluoride source and 95-5% of said hydantoin.

9. The composition of claim 1, wherein said fluoride source and said hydantoin together comprise a hydantoin with a fluoride substituent.

10. A method of increasing the rate of bone formation, which comprises:
administering to a vertebrate in need thereof a combination of a fluoride source capable of releasing fluoride ions in a physiological environment and a mitogenic hydantoin comprising a hydantoin having an aromatic substituent at position 5 in an amount sufficient to increase the rate of bone formation in said vertebrate wherein said fluoride source provides a molar ratio of fluoride ion to hydantoin of from about 0.1:1 to about 100:1.

11. The method of claim 10, wherein said fluoride source is an alkali metal fluoride salt, an alkaline earth metal fluoride salt, an alkali metal monofluorophosphate salt, or an alkaline earth metal monofluorophosphate salt.

12. The method of claim 11, wherein said hydantoin is a compound of the formula:

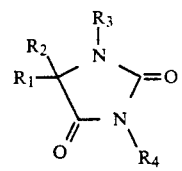

wherein R₁ is an organic substituent selected from the group consisting of substituted and unsubstituted 5-and 6-membered aromatic rings containing 0-3 nitrogen ring atoms or 0-1 oxygen or sulfur ring atoms and said aromatic rings are attached to the hydantoin ring of said formula through an intervening substituted or unsubstituted hydrocarbyl group containing from 1 to 3 carbon atoms; R₂ is R₁, a C₁-C₄ hydrocarbyl group or H; R₃ is a C₁-C₄ hydrocarbyl group or H; and R₄ is a C₁-C₄ hydrocarbyl group or H; or a pharmaceutically acceptable salt thereof.

13. The method of claim 12, wherein said fluoride source is a sodium salt and in said hydantoin R₁ comprises a phenyl or a phenyl substituted with a C₁-C₄ alkyl, hydroxyl, carboxyl or amino group or an amino group substituted with one or two C₁-C₄ alkyl, R₂ is R₁, a C₁-C₄ alkyl group or H; R₃ is H; and R₄ is a C₁-C₄ alkyl group or H; or a pharmaceutically acceptable salt thereof.

14. The method of claim 13, wherein R₁ is phenyl or said substituted phenyl; R₂ is R₁, a C₁-C₄ alkyl group or H; and R₄ is methyl, ethyl or H; or a lithium, sodium or potassium salt thereof.

15. The method of claim 14, wherein said hydantoin is phenytoin, phenytoin sodium, mephenytoin or ethotoin.

16. The method of claim 15, wherein said fluoride source is NaF or Na₂PO₃F.

17. The method of claim 11, wherein said amounts comprise 0.15-15 mg fluoride and 0.1-2.0 mmole hydrantoin perkilogram of body weight.

18. The method of claim 11, wherein said combination is administered orally, parenterally, or by a subcutaneous, transdermal, or nasal route.

* * * * *